United States Patent [19]

Ozawa et al.

[11] 4,255,447
[45] Mar. 10, 1981

[54] ACARICIDAL COMPOUNDS OF CYCLOPROPANE CARBOXYLIC ACID DERIVATIVES

[75] Inventors: Kiyomi Ozawa; Shigeru Ishii, both of Funabashi; Mamoru Hayashi, Shiraoka; Masayoshi Hirose, Shiraoka; Kiminori Hirata, Shiraoka, all of Japan

[73] Assignee: Nissan Chemical Industries Limited, Tokyo, Japan

[21] Appl. No.: 65,340

[22] Filed: Aug. 9, 1979

[30] Foreign Application Priority Data

Sep. 12, 1978 [JP] Japan ................... 53-112107

[51] Int. Cl.³ ..................... A01N 53/00; C07C 121/75
[52] U.S. Cl. ................... 424/304; 260/465 D
[58] Field of Search ................... 260/465 D; 424/304

[56] References Cited

U.S. PATENT DOCUMENTS 3,567,740  3/1971  Matsui et al. ................... 560/124
3,835,176  9/1974  Matsuo et al. ................... 260/465 D
3,850,977  11/1974  Itaya et al. ................... 560/124

Primary Examiner—Dolph H. Torrence
Attorney, Agent, or Firm—Oblon, Fisher, Spivak, McClelland & Maier

[57] ABSTRACT

Phenylcyclopropane carboxylic acid derivatives having the formula (I)

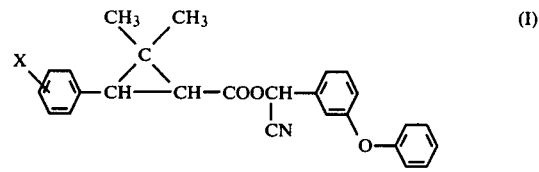

wherein X represents a $C_2$–$C_{10}$ straight or branched alkyl group, are novel compounds having excellent acaricidal effect.

11 Claims, No Drawings

ACARICIDAL COMPOUNDS OF CYCLOPROPANE CARBOXYLIC ACID DERIVATIVES

BACKGROUND OF THE INVENTION

The present invention relates to novel cyclopropane carboxylic acid derivatives having the formula

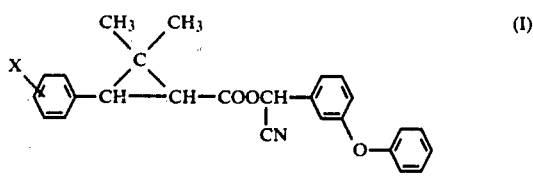

wherein X represents a $C_2$-$C_{10}$ straight or branched alkyl group and acaricidal compositions containing the same.

The compounds of the present invention are novel compounds which have excellent acaricidal effect.

Various acarina in various growth stages such as mago, larva and ovum are found as parasitic acarina on fruit trees, vegetables, flowers and woods.

Various acaricidal compositions used for controlling acarina have been developed and tested. However, effect of the acaricide is different depending upon the kinds and growth stages of the acarina. Various active ingredients have been applied depending upon characteristics of the active ingredients and applicating places. Moreover, the development of novel acaricides have been required in view of prevention of resistance of acarina to acaricides which is caused by continuous applications of specific acaricides.

The inventors have studied to develop novel acaricides which are different from the known acaricides.

Heretofore, certain phenylcyclopropane carboxylic acid derivatives have been known.

The compounds having the formula

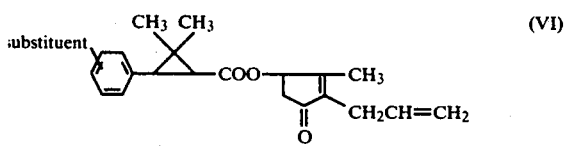

have been known in Collection of Czechoslovak Chemical Communication, 24, 2460 (1959) and 25, 1815 (1960).

These compounds are carboxylic acid esters having

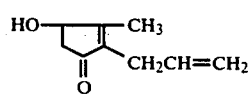

as the alcohol moiety. However, insecticidal activity of the compounds for houseflies is only similar to that of allethrin of one of the commerciallized pyrethroids when the substituent on the phenyl group is a hydrogen atom and the insecticidal activity is inferior when the substituent on the phenyl group is chlorine, or fluorine atom or methyl or methoxy group (no acaricidal activity is described).

The compounds having the formula

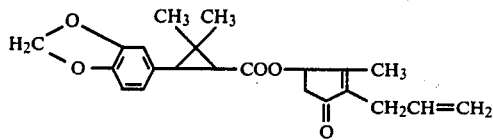

has been disclosed in Bochu Kagaku Vol. 27, III, page 51 (1962). However, the insecticidal activity of the compound is only similar to that of allethrin.

The inventors have checked a phenylcyclopropane carboxylic acid ester illustrated below.

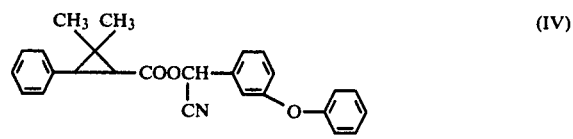

This compound has no substituent on phenyl group. However, an acaricidal activity of this compound is quite low.

SUMMARY OF THE INVENTION

It is an object of the present invention to provide novel acaricidal compounds which have high acaricidal effects and low toxicity to mammals and fishes.

Another object of the present invention is to provide a new use of novel acaricidal compounds of phenylcyclopropane carboxylic acid derivatives.

The other objects of the present invention is to provide a process for producing the acaricidal compound of phenylcyclopropane carboxylic acid derivatives.

Briefly, the foregoing and other objects of the present invention have been attained by providing acaricidal compounds of phenylcyclopropane carboxylic acid derivatives having the formula

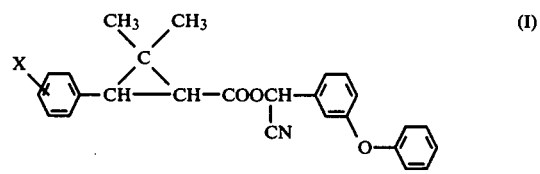

wherein X represents a $C_2$-$C_{10}$ straight or branched alkyl group.

DETAILED DESCRIPTION OF THE PREFERRED EMBODIMENTS

The novel acaricidal compounds of phenylcyclopropane carboxylic acid derivatives having the formula (I) have excellent acaricidal effects, because of the substituent on phenyl group. The acaricidal activity of the acaricidal compounds of the present invention is significant.

The acaricides of the present invention are mainly applied to parasitic acarina on fruit trees and vegetables such as carmine mite (*Tetranychus cinnabarinus*), Kanzawa spider mite (*Tetranychus kanzawai*), two-spotted mite (*Tetranychus urticae*), citrus red mite (*Panonychus citri*), Japanese citrus rust mite (*Aculus pelekassi*), European red mite (*Panonychus ulmi*), sweet cherry spider mite (*Tetranychus viennensis*) etc. and are also effective for the other plant parasitic acarina which cause damage to agricultural horticultural plants and forests and are also applicable to various animal parasitic acarina and other acarina.

The novel compounds of the present invention also have certain insecticidal activity to various insects injurious to sanitation as well as agriculture, especially house fly, green rice leafhopper and rice stem borer.

It has been well known that pyrethrins and synthetic pyrethroids have high toxicity to fishes and shell-fishes (TLM: less than 0.1 ppm to Killifish). On the contrary, TLM in 48 hours for the acaricidal compounds of the present invention are approximately 20 ppm to Killifish.

It is an unexpected result from the conventional knowledge that the acaricidal compounds of the present invention have excellent acaricidal activity and significant low toxicity.

The process for producing the novel acaricidal compounds will be illustrated by the following schemes.

In the schemes (A) to (D), the references X is defined above and Y represents a halogen atom or sulfonate group and Hal represents a halogen atom.

In the process (A), an organic tertiary base such as pyridine and triethylamine or an inorganic base such as alkali metal or alkaline earth metal hydroxides is used as the dehydrogen halide agent and the starting materials are reacted in an inert solvent such as benzene.

In the process (B), the starting components are reacted in an inert solvent such as acetonitrile in the presence of a dehydrating agent such as dicyclohexylcarbodiimide. Alternatively, p-toluene-sulfonic acid or conc. sulfuric acid used in an esterification can be used as the catalyst.

In the process (C), the starting materials are reacted in a solvent such as dimethylformamide, preferably under refluxing. In the course of the reaction, an alkali metal or alkaline earth metal hydroxide is used for converting an acid to a salt such as potassium or sodium salt etc.

In the process (D), the starting materials are reacted in an aprotic solvent which is not miscible to water such as n-heptane in the presence of water soluble cyan com-

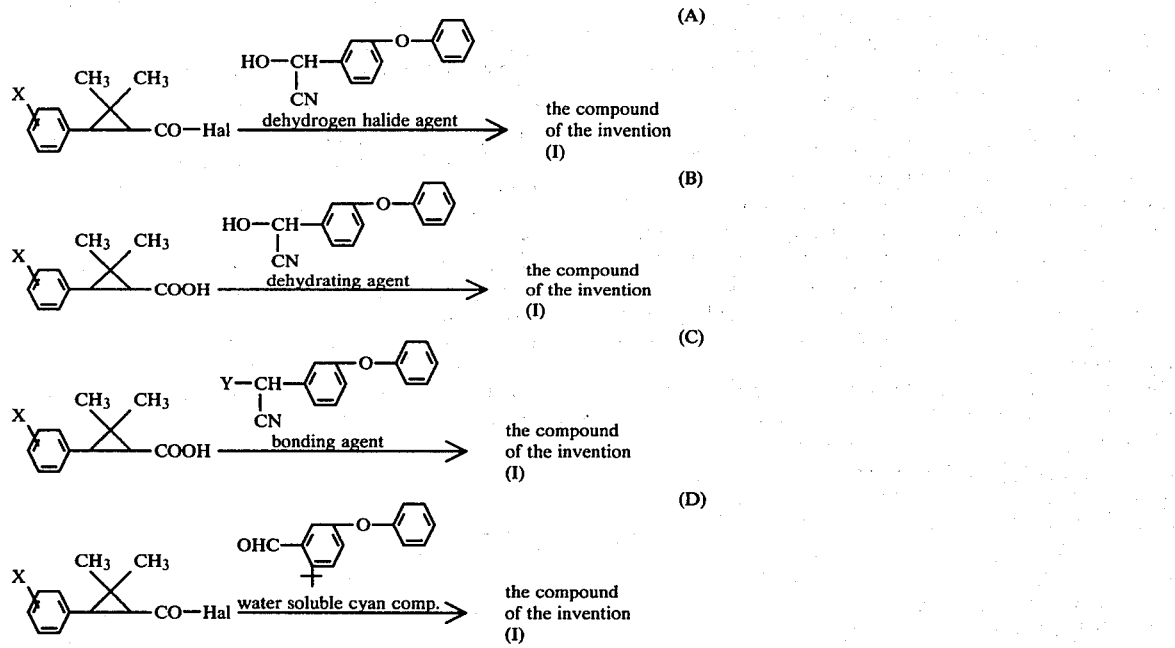

The acaricidal compounds of the present invention can be obtained in high yield by the processes of (A) to (D).

The processes are further illustrated in detail as follows.

pound such as sodium cyanide and a phase transfer catalyst such as tetra-n-butyl ammonium chloride or trimethyl benzyl ammonium chloride to obtain the object compound of the present invention in high yield.

Typical compounds of the present invention will be shown in the following list.

TABLE

| Compound No. | Structure | Refractive index |
|---|---|---|
| 1 | (CH3)3C—⌬—⋊(CH3)(CH3)—COOCH(CN)—⌬—O—⌬ | $N_D^{20} = 1.5612$ |
| 2 | (CH3)2CH—⌬—⋊(CH3)(CH3)—COOCH(CN)—⌬—O—⌬ | $N_D^{20} = 1.5831$ |

TABLE-continued

| Compound No. | Structure | Refractive index |
|---|---|---|
| 3 | CH₃CH₂—⟨benzene⟩—C(CH₃)(CH₃)(cyclopropane)—COOCH(CN)—⟨benzene⟩—O—⟨benzene⟩ | $N_D^{20} = 1.5709$ |
| 4 | CH₃CH₂C(CH₃)(CH₃)—⟨benzene⟩—C(CH₃)(CH₃)(cyclopropane)—COOCH(CN)—⟨benzene⟩—O—⟨benzene⟩ | $N_D^{23.5} = 1.5589$ |
| 5 | CH₃CH₂CH₂CH₂—⟨benzene⟩—C(CH₃)(CH₃)(cyclopropane)—COOCH(CN)—⟨benzene⟩—O—⟨benzene⟩ | $N_D^{23.5} = 1.5614$ |
| 6 | (CH₃)₂CHCH₂—⟨benzene⟩—C(CH₃)(CH₃)(cyclopropane)—COOCH(CN)—⟨benzene⟩—O—⟨benzene⟩ | $N_D^{23.5} = 1.5607$ |
| 7 | CH₃CH₂CH(CH₃)—⟨benzene⟩—C(CH₃)(CH₃)(cyclopropane)—COOCH(CN)—⟨benzene⟩—O—⟨benzene⟩ | $N_D^{23.5} = 1.5589$ |
| 8 | (CH₃)₃C—⟨benzene⟩—C(CH₃)(CH₃)(cyclopropane)—COOCH(CN)—⟨benzene⟩—O—⟨benzene⟩ | $N_D^{23.5} = 1.5590$ |
| 9 | (CH₃)₃C—⟨benzene⟩—C(CH₃)(CH₃)(cyclopropane)—COOCH(CN)—⟨benzene⟩—O—⟨benzene⟩ (cis form) | $N_D^{23.5} = 1.5561$ |
| 10 | CH₃(CH₂)₈CH₂—⟨benzene⟩—C(CH₃)(CH₃)(cyclopropane)—COOCH(CN)—⟨benzene⟩—O—⟨benzene⟩ | $N_D^{23.5} = 1.5476$ |

The cyclopropane carboxylic acid derivatives of the present invention include, of course, optical isomers thereof due to the assymetric carbon atom of the carboxylic acid moiety and the alcohol moiety, and geometrical isomers thereof due to the stereo structure of the carboxylic acid moiety.

Certain examples of syntheses of the compounds of the present invention will be illustrated below.

PREPARATION 1

Preparation of Compound No. 1

Into 20 ml. of benzene, 2.3 g. of α-cyano-m-phenoxybenzyl alcohol and 0.8 g. of pyridine were dissolved. The solution was stirred under cooling with ice and 2.7 g. of trans-2,2-dimethyl-3-(p-t-butyl-phenyl)-cyclopropane carboxylic acid chloride was added dropwise to the solution. After reacting them for 1 hour, the product was washed twice with 10 ml. of water and the organic layer was dried over anhydrous sodium sulfate and benzene was distilled off under a reduced pressure. The residual oily product was purified by a column chromatography (alumina: developing solvent benzene) giving 4.3 g. of the object compound.

NMR spectrum: δ,ppm, CCl₄; 0.90 (3H, bs); 1.24 (9H, S); 1.24 (1.5H, S); 1.39 (1.5H, S); 1.92 (1H, d,J=6.0 Hz); 2.65 (1H, d,J=6.0 Hz); 6.28 (0.5H, S); 6.33 (0.5H, S); 6.75 to 7.40 (13H, m).

PREPARATION 2

Preparation of Compound No. 2

A mixture of 4 g. of m-phenoxybenzaldehyde, 5.0 g. of trans-2,2-dimethyl-3-(p-isopropylphenyl)-cyclopropane carboxylic acid chloride, 1.2 g. of sodium cyanide, 3.0 ml. of water, 0.3 g. of tetra-n-butyl-ammonium chloride and 40 ml. of n-heptane were vigorously stirred at room temperature to react them for 40 hours. After reacting them, the resulting precipitate was filtered off and the filtrate was washed with an aqueous solution of sodium bicarbonate, with an aqueous solution of sodium hydrogen sulfite and with water and the organic layer was dried over anhydrous sodium sulfate and n-heptane was distilled off under a reduced pressure from the organic layer giving the object compound as a crude ester. The product was purified by a silica gel chromatography (n-hexane: ethyl acetate=4:1) giving 7.0 g. of the object compound.

NMR spectrum: δ, ppm, CCl₄; 0.98 (3H, bs); 1.17 (6H, d,J=7.0 Hz); 1.25 (1.5H, S); 1.37 (1.5H, S); 1.90 (1H, d,J=6.0 Hz); 2.64 (1H, d,J=6.0 Hz); 2.80 (1H, qq. J=7.0 Hz); 6.28 (0.5H, S); 6.37 (0.5H, bs); 6.70 to 7.60 (13H, m).

PREPARATION 3

Preparation of Compound No. 7

Into 20 ml. of n-hexane, 2 g. of m-phenoxybenzaldehyde, 2.6 g. of trans-2,2-dimethyl-3-(p-sec-butylphenyl)-cyclopropane carboxylic acid chloride, 0.6 g. of sodium cyanide, 1.5 ml. of water and 0.1 g. of tetra-n-butyl ammonium chloride were added and the mixture was vigorously stirred at room temperature to react them for 24 hours.

After reacting them, 100 ml. of ethyl ether was added and the organic layer was separated and washed with an aqueous solution of sodium bisulfite and then with water and dried over anhydrous sodium sulfate and n-hexane was distilled off under a reduced pressure from the organic layer giving the object compound as a crude ester. The product was purified by a column chromatography (alumina: developing solvent of benzene) giving 3.7 g. of the object compound.

NMR spectrum: $\delta$, ppm, $CCl_4$; 1.82 (3H, q.J=7.0 Hz); 1.85 (3H, bs); 1.18 (3H, d,J=7.0 Hz); 1.28 (1.5H, S); 1.38 (1.5H, S); 1.50 (2H, m); 1.91 (1H, d,J=6.0 Hz); 2.38 (1H, m); 2.65 (1H, d,J=6.0 Hz); 6.22 (0.5 H, S); 6.30 (0.5H, S); 6.75 to 7.30 (13H, m).

PREPARATION 4

Preparation of Compound No. 9

A mixture of 2 g. of m-phenoxybenzaldehyde, 2.6 g. of cis-2,2-dimethyl-3-(p-t-butylphenyl)-cyclopropane carboxylic acid chloride, 0.6 g. of sodium cyanide, 1.5 ml. of water, 0.1 g. of tetra-n-butyl ammonium chloride and 20 ml. of n-heptane was vigorously stirred at room temperature to react them. The crude product, obtained according to the procedure similar to that of Preparation 3, was purified by a column chromatography (alumina; developing solvent of n-hexane) to obtain 4.1 g. of the object compound.

NMR spectrum: $\delta$, ppm, $CCl_4$; 1.21 to 1.31 (6H, m); 1.28 (9H, S); 1.80 (1H, d,J=9.0 Hz); 2.41 (1H, m); 6.17 (1H, S); 6.75 to 7.30 (13H, m).

PREPARATION 5

Preparation of Compound No. 1 ($[\alpha]_D^{20} = +20.2$)

Into 100 ml. of 60% ethanol aqueous solution, 4.8 g. of ($\pm$) trans-2,2-dimethyl-3-(p-t-butylphenyl)-cyclopropane carboxylic acid and 2.5 g. of ($-$)-$\alpha$-methylbenzylamine were added and dissolved by heating. The solution was kept at room temperature for one night and the precipitated crystals were separated by a filtration. The resulting crystals were recrystallized two times from an ethanol-aqueous solution and also recrystallized two times from ethyl acetate and further recrystallized from 60% ethanol-aqueous solution to obtain 2.2 g. of the crystals.

The crystals were decomposed in 10% sulfuric acid. The product was extracted with ether and dried over anhydrous sodium sulfate. Ether was distilled off to obtain 1.47 g. of trans-2,2-dimethyl-3-(p-t-butylphenyl)-cyclopropane carboxylic acid having (+) predominant optical rotary power ($[\alpha]_D^{20}:+41.2$ ($CHCl_3$) and melting point: 117°–119° C.).

In 10 ml. of benzene, 0.74 g. of the carboxylic acid and 0.39 g. of thionyl chloride were reacted at 50° C. to obtain 0.78 g. of the carboxylic acid chloride.

In accordance with the process of Preparation 2 except using the resulting acid chloride, the process for the production was repeated to obtain 0.35 g. of the Compound 1 ($[\alpha]_D^{20}:+20.2$ and $n_D^{20}:1.5782$).

The Compound No. 1 ($[\alpha]_D^{20} = +20.2$) was tested in accordance with the test methods of Experiment 1 and 2 described below. The Percent mortalities of two spotted mite and carmine mite in the case of Compound No. 1 $[\alpha]_D^{20} = +20.2$ were superior to those of the Compound No. 1 (racemic form).

When the compounds of this invention is used as an acaricidal composition, suitable adjuvant is admixed with the acaricidal compound at suitable ratio to dissolve, to disperse, to suspend, to blend, to immerse, to adsorb or to adhere the acaricidal compound so as to form suitable composition in a form of a solution, a dispersion, an emulsion, an oil spray, a wettable powder, a dust, a granule, a pellet, a paste or an aerosol. The adjuvants include emulsifiers, dispersing agents, suspending agents, penetrants, spreaders and stabilizers.

In the acaricidal composition, the aricacide of the present invention can be blended to suitable other ingredients such as other acaricides, insecticides, fungicides, herbicides, plant growth regulators, attractant-synergists, repellents and perfumes.

The stability of the compound of the present invention can be improved by combining an antioxident such as phenol type antioxidants e.g. 2,6-di-t-butyl-4-methylphenol (B.H.T.) and 2,6-di-t-butylphenol and amine type antioxidants.

Certain acaricidal compositions containing the compound of the present invention will be illustrated as follows.

COMPOSITION 1

Emulsifiable concentrate:

| | |
|---|---|
| Compound No. 1 | 20 wt. parts |
| Xylol | 65 wt. parts |
| Sorpol 2680 (Toho Chem.) | 15 wt. parts |

The components were uniformly mixed and was diluted with 500 to 2,000 times the quantity of water and the aqueous solution was sprayed in amounts of 50 to 800 liter/10 ares.

COMPOSITION 2

Wettable powder:

| | |
|---|---|
| Composition No. 1 | 20 wt. parts |
| Zeeklite | 75 wt. parts |
| Sorpol 8048 (Toho Chem.) | 3 wt. parts |
| Runox 1000 (Toho Chem.) | 2 wt. parts |

The components were uniformly mixed to obtain a wettable powder.

The wettable powder was diluted with 500 to 2,000 times of the quantity of water and the dispersion was sprayed in amounts of 50 to 800 liter/10 ares.

The following is certain experiments which were conducted with the compositions of the present invention.

As references, the following active ingredients were used instead of the compound of the present invention.

Reference Compound A:

-continued

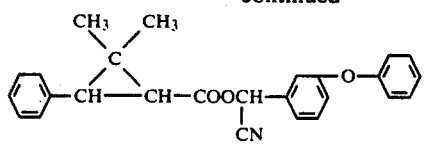

Tricyclohexyl tin-hydroxide:

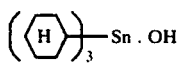

Dimethoate:

Amitraz:

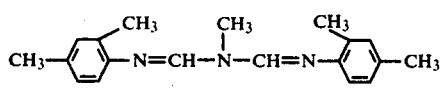

Reference Compound B:

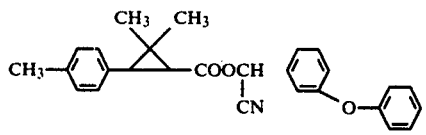

EXPERIMENT 1

Test for killing two-spotted mite

Leaves of kidney bean was cut by a leaf-punch in a form of circle having a diameter of 1.5 cm. The leaf-discs were put on a wet filter paper on a polystyrene cup. Ten of two-spotted mites were inoculated on the leaf-discs in the cup. Half days after the inoculation, each solution prepared by diluting each emulsifiable concentrate of the present invention or each control with a spreader at each predetermined concentration was sprayed by a rotary spray for 2 ml. per each cup.

Numbers of mortalities of two-spotted mites were measured after 24 hours or 48 hours from the spraying and percent mortalities were calculated.

The tests were carried out in two groups. The results are shown in Table 1.

EXPERIMENT 2

Test for killing carmine mites

In accordance with the method of Experiment 1, percent mortalities of carmine mites were measured. The results are shown in Table 1.

EXPERIMENT 3

Test for killing citrus red mites

In accordance with the method of Experiment 1 except using leaves of Unshu orange, percent mortalities of citrus red mites were measured. The results are shown in Table 1.

EXPERIMENT 4

Residual test against two-spotted mites

In each pot having a diameter of 12 cm., kidney bean was grown and parasitic two-spotted mites were inoculated on a leaf. The natural proliferation of the mites were allowed for 8 days and then each solution prepared by diluting each emulsifiable concentrate of the present invention and each control with a spreader at each predetermined concentrate was sprayed by a spray to wet the leaves. After drying it in air, it was maintained in a green house. Numbers of mites were measured after the specific days. The parasitic acarina index was calculated by the equation.

$$\text{parasitic acarina index} = \frac{\text{number of parasitic acarina after spraying}}{\text{number of parasitic acarina before spraying}} \times 100$$

The results are shown in Table 2.

EXPERIMENT 5

Residual test against carmine mites

In accordance with the method of Experiment 4, tests were carried out. The results are shown in Table 2.

EXPERIMENT 6

Residual test against citrus red mites

In accordance with the method of Experiment 4, except using seedlings of Summer orange tests were carried out. The results are shown in Table 3.

TABLE 1

| | | Test for killing acarina | | | | | |
|---|---|---|---|---|---|---|---|
| | | Percent mortality (%) | | | | | |
| | | two-spotted mite | | carmine mite | | citrus red mite | |
| Compound | Concentration (%) | 24 hr. | 48 hr. | 24 hr. | 48 hr. | 24 hr. | 48 hr. |
| Compound No. 1 | 0.05 | 100 | 100 | 100 | 100 | 30 | 70 |
| | 0.01 | 70 | 80 | 90 | 100 | 10 | 30 |
| Compound No. 2 | 0.05 | 80 | 100 | 100 | 100 | 50 | 70 |
| | 0.01 | 50 | 60 | 100 | 100 | 40 | 50 |
| Compound No. 4 | 0.03 | — | — | 100 | 100 | — | — |
| | 0.009 | — | — | 60 | 90 | — | — |
| Compound No. 5 | 0.03 | 65 | 75 | 65 | 80 | — | — |
| | 0.009 | — | — | 40 | 50 | — | — |
| Compound No. 6 | 0.03 | — | — | 80 | 100 | — | — |
| | 0.009 | — | — | 80 | 80 | — | — |
| Compound No. 7 | 0.03 | 100 | 100 | 100 | 100 | — | — |
| | 0.009 | — | — | 65 | 95 | — | — |
| Reference Compound A | 0.01 | — | — | 45 | 55 | — | — |
| Reference Compound B | 0.03 | 30 | 35 | — | — | — | — |
| | 0.009 | 10 | 15 | — | — | — | — |
| Non-treatment | — | 0 | 0 | 0 | 0 | 0 | 0 |

TABLE 2

| | | Test for controlling parasitic acarina | | | | | | | |
| --- | --- | --- | --- | --- | --- | --- | --- | --- | --- |
| | | Parasitic acarina index | | | | | | | |
| | | two-spotted mite | | | carmine mite | | | citrus red mite | | |
| | Concentration | Days | | | Days | | | Days | | |
| Compound | (%) | 3 | 7 | 14 | 3 | 7 | 14 | 3 | 7 | 14 |
| Compound No. 1 | 0.01 | 3 | 0 | 2 | 0 | 4 | 43 | 3 | 0 | 21 |
| Compound No. 3 | 0.02 | — | — | — | 3 | 1 | 50 | — | — | — |
| Reference Tricyclohexyl tin-hydroxide | 0.01 | 6 | 0 | 24 | — | — | — | — | — | — |
| Dimethoate | 0.01 | — | — | — | 263 | 493 | >1000 | — | — | — |
| Amitraz | 0.01 | — | — | — | — | — | — | 0 | 1 | 3 |
| Non-treatment | — | 142 | 347 | 632 | 391 | 230 | >1000 | 61 | 26 | 42 |

As its is clearly understood from the results shown in Table 1, the compounds of the present invention have excellent acaricidal effects to two-spotted mite, carmine mite and citrus red mite, which are remarkably superior to that of the analogous compound of Compound A.

As shown in Table 2, the compounds of the present invention have excellent residual effects against acarina. After 14 days from the application of the acaricide, to two-spotted mite, the compounds of the present invention impart remarkably superior acaricidal effect to the commercial acaricidal product of tricyclohexyl-tin hydroxide. The compounds of the present invention impart remarkably superior controlling effect to carmine mites which are resistant to organophosphorus compounds as the reference, Dimethoate.

The novel compounds of the present invention are useful as acaricides.

We claim:

1. An acaricidal compound of phenylcyclopropane carboxylic acid derivatives having the formula

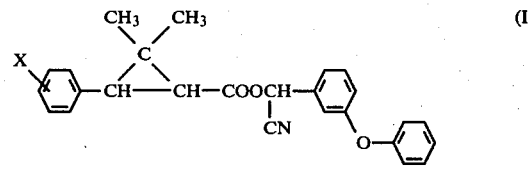

wherein X represents a $C_2$–$C_{10}$ straight or branched alkyl group.

2. An acaricidal compound of phenylcyclopropane carboxylic acid derivative having the formula

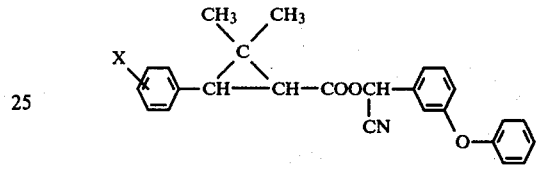

wherein X represents propyl or butyl group.

3. An acaricidal compound of phenylcyclopropane carboxylic acid derivative having the formula

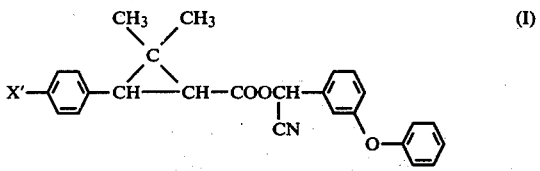

wherein X' represents isopropyl group, t-butyl group or sec-butyl group.

4. An acaricidal composition which comprises an acaricidal compound of phenylcyclopropane carboxylic acid derivative having the formula (I) and an adjuvant in a form of a solution, a dispersion, an emulsion, an oil spray, a wettable powder, a dust, a granule, a tablet, a pellet, a paste or an aerosol.

5. An acaricidal composition according to claim 4 which comprises said acaricidal compound of phenylcyclopropane carboxylic acid derivative having the formula (I) and an antioxidant.

6. The compound of claim 1, wherein X is $(CH_3)_3C$—.

7. The compound of claim 1, wherein X is $(CH_3)_2CH$—.

8. The compound of claim 1, wherein X is $CH_3CH_2\overset{|}{C}(CH_3)_2$.

9. The compound of claim 1, wherein X is $CH_3(CH_2)_3$—.

10. The compound of claim 1, wherein X is $(CH_3)_2CHCH_2$—.

11. The compound of claim 9, wherein X is $CH_3CH_2\overset{|}{C}H(CH_3)$.

* * * * *